United States Patent
Wang et al.

(10) Patent No.: US 10,316,351 B2
(45) Date of Patent: *Jun. 11, 2019

(54) DNA QUALITY ASSESSMENTS USING REPETITIVE SEQUENCES

(71) Applicant: QIAGEN Sciences, LLC, Germantown, MD (US)

(72) Inventors: Yexun Wang, Ellicott City, MD (US); John DiCarlo, Frederick, MD (US); Vikram Devgan, Frederick, MD (US); Qiong Jiang, Frederick, MD (US); Quan Peng, Rockville, MD (US)

(73) Assignee: QIAGEN Sciences, LLC, Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/919,640

(22) Filed: Mar. 13, 2018

(65) Prior Publication Data

US 2018/0208971 A1  Jul. 26, 2018

Related U.S. Application Data

(63) Continuation of application No. 14/208,460, filed on Mar. 13, 2014, now Pat. No. 9,963,736.

(60) Provisional application No. 61/783,225, filed on Mar. 14, 2013.

(51) Int. Cl.
| | |
|---|---|
| *C12P 19/34* | (2006.01) |
| *C12Q 1/6806* | (2018.01) |
| *C12Q 1/6851* | (2018.01) |

(52) U.S. Cl.
CPC .......... *C12Q 1/6806* (2013.01); *C12Q 1/6851* (2013.01); *C12Q 2537/143* (2013.01); *C12Q 2543/10* (2013.01)

(58) Field of Classification Search
None
See application file for complete search history.

(56) References Cited

U.S. PATENT DOCUMENTS

| | | |
|---|---|---|
| 2006/0210980 A1 | 9/2006 | Cawthon |
| 2008/0206755 A1 | 8/2008 | Sinha et al. |
| 2009/0280479 A1 | 11/2009 | Hoon et al. |
| 2014/0051075 A1 | 2/2014 | Sinha |

FOREIGN PATENT DOCUMENTS

WO    2011/150110 A1    12/2011

OTHER PUBLICATIONS

Altschul et al., "Basic Local Alignment Search Tool," *J. Mol. Biol.* 215:403-410 (1990).
Altschul et al., "Local Alignment Statistics," *Methods in Enzymology* 266:460-480 (1996).
Karlin et al., "Applications and statistics for multiple high-scoring segments in molecular sequences," *Proc. Natl. Acad. Sci. USA*, 90:5873-5877 (1993).
Mamanova et al., "Target-enrichment strategies for next-generation sequencing," *Nature Methods* 7(2):111-118 (2010).
Nguyen-Hieu et al., "Heat degradation of eukaryotic and bacterial DNA: an experimental model for paleomicrobiology," *BMC Research Notes* 5:528 (2012).
Opel et al., "Evaluation and Quantification of Nuclear DNA from Human Telogen Hairs," *Journal of Forensic Sciences* 53(4):853-857 (2008).
Qiagen, "qBiomarker Somatic Mutation PCR Handbook," (60 pages) (Aug. 2012).
Qiagen, "Appendix C: Quality Control Using the qBiomarker Somatic Mutation PCR Array Human DNA QC Plate," qBiomarker Somatic Mutation PCR Handbook, pp. 47-52 (Aug. 2012), XP-002724675, Retrieved from the Internet: URL:http://www.sabiosciences.com/Manual/1073788, [Retrieved on May 21, 2014].
Sah et al., "Functional DNA quantification guides accurate next-generation sequencing mutation detection in formalin-fixed, paraffin-embedded tumor biopsies," *Genome Medicine* 5:77 (12 pages) (2013).
San Gabriel et al., "Estimation of human sperm gene-specific deoxyribonucleic acid damage by real-time polymerase chain reaction analysis," *Fertility and Sterility* 85(3):797-799 (2006).

*Primary Examiner* — Kenneth R Horlick

(74) *Attorney, Agent, or Firm* — Seed IP Law Group LLP

(57) ABSTRACT

The present disclosure provides methods, arrays and kits for assessing the quality of genomic DNA samples, especially those obtained from formalin-fixed paraffin-embedded (FFPE) samples. The methods, arrays and kits provided herein use primer pairs specific to regions in the genomes of the organisms from which genomic DNA samples are obtained that have identical or nearly identical copies distributed across multiple chromosomes.

18 Claims, 3 Drawing Sheets

Specification includes a Sequence Listing.

Fig. 1

DNA QUALITY ASSESSMENTS USING REPETITIVE SEQUENCES

CROSS REFERENCE TO RELATED APPLICATIONS

The present application is a continuation application of U.S. application Ser. No. 14/208,460 filed Mar. 13, 2014, issued on May 8, 2018, as U.S. Pat. No. 9,963,736, which claims priority to U.S. Provisional Application No. 61/783,225 filed Mar. 14, 2013. U.S. application Ser. No. 14/208,460 is herein incorporated by reference in its entity.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 830109_404C1_SEQUENCE_LISTING.txt. The text file is 4.6 KB, was created on Jan. 7, 2018, and is being submitted electronically via EFS-Web.

BACKGROUND

Technical Field

The present disclosure relates to methods, arrays and kits for assessing the quality of DNA samples.

Description of the Related Art

DNA has become biomarkers with the most potential. Compared to other biomarkers, DNA is stable and has less dynamic change. In addition, DNA as biomarkers is sequence based and has less ambiguity. Recently, discovery of DNA as biomarkers has been propelled by the growing application of next generation sequencing (NGS).

The quality of any scientific data is directly proportional to that of the starting samples. It is important to assess the quality of a starting DNA sample for downstream molecular analyses, such as qPCR assays and NGS. A bad quality sample will generate unusable data, which causes waste in material and labor. Not knowing the DNA quality can also lead to misuse of precious sample, which once used, cannot be recovered.

Various methods are known for DNA quality evaluation. Most commonly used spectrometrical methods can address some of the questions in DNA concentration and contaminants. However, it cannot detect many contaminants easily or evaluate the actual impact of contaminants in the molecular assays. Electrophoresis can evaluate the sizes of DNA sample. However, it cannot evaluate base damages, cross-linkage, modifications, which can adversely affect downstream enzymatic assays. Other people select to test a group of gene assays in PCR to estimate actual sample performance in molecular assays. However, selection of a few gene assays is sometimes biased, affected by biological changes in local chromosomal structure (as seen in pathological conditions) and does not have broader representations. Thus, the prediction for a performance of DNA samples in downstream molecular applications has been challenging, especially for DNA extracted from formalin-fixed paraffin-embedded (FFPE) samples. Accordingly, there is a need to establish an objective method to evaluate the quality of DNA for downstream DNA analyses.

SUMMARY

In one aspect, the present disclosure provides a method for assessing the quality of a test genomic DNA sample, comprising:

(a) performing one or more real-time PCR reactions that use genomic DNA in a test genomic DNA sample as templates in the presence of one or more primer pairs, wherein each of the one or more primer pairs is specific for amplifying identical or nearly identical genomic DNA fragments that are present at multiple locations in the genome of the organism from which the DNA sample is obtained, (b) performing one or more real-time PCR reactions that use genomic DNA in a control genomic DNA sample as templates in the presence of the one or more primer pairs used in step (a), (c) determining the Ct values for the one or more real-time PCR reactions in step (a), and (d) determining the Ct values for the one or more real-time PCR reactions in step (b), wherein the difference between the Ct values determined in step (c) and the corresponding Ct values determined in step (d) for the one or more real-time PCR reactions are indicative of the quality of the test genomic DNA sample.

In certain embodiments, the number of the primer pairs is 4-8.

In certain embodiments, the genomic DNA fragments amplified in the presence of each primer pair are present at 10 or more different locations in the genome of the organism from which the DNA sample is obtained.

In certain embodiments, the genomic DNA fragments amplified in the presence of each primer pair in combination are present in more than 80% of all autosomes of the organism from which the DNA sample is obtained.

In certain embodiments, the test genomic DNA sample is obtained from human cells or tissue.

In certain embodiments, the test genomic DNA sample is obtained from a clinical sample.

In certain embodiments, the test genomic DNA sample is obtained from a formalin fixed and paraffin-embedded (FFPE) sample.

In certain embodiments, the genomic DNA fragments amplified in step (a) are between about 100 to 400 bp in length.

In certain embodiments, the genomic DNA fragments amplified in step (a) are of at least 2 substantially different sizes.

In certain embodiments, multiple real-time PCR reactions are performed in each of steps (a) and (b), and the average difference between the Ct values determined in step (c) and the corresponding Ct values determined in step (d) for two or more of the multiple real-time PCR reactions is used to assess the quality of the test genomic DNA sample.

In certain embodiments, the primer pairs are selected from the following primer pairs: (1) SEQ ID NOS:1 and 2, (2) SEQ ID NOS:3 and 4, (3) SEQ ID NOS:5 and 6, (4) SEQ ID NOS:7 and 8, (5) SEQ ID NOS:9 and 10, (6) SEQ ID NOS:11 and 12, (7) SEQ ID NOS:13 and 14, (8) SEQ ID NOS:15 and 16, (9) SEQ ID NOS:17 and 18, (10) SEQ ID NOS:19 and 20, and (11) SEQ ID NOS:21 and 22, (12) SEQ ID NOS:23 and 24.

In certain embodiments, the method further comprises performing additional real-time PCR and/or NGS analysis of the test genomic DNA sample.

In another aspect, the present disclosure provides an array for assessing the quality of a test genomic DNA sample, comprising a solid support and multiple compartments in the solid support, wherein a first primer pair specific to a first genomic DNA fragment in the test genomic DNA sample is contained in a first compartment or each of a first set of compartments, and wherein (a) the first genomic DNA fragment and (b) one or more fragments nearly identical to the first genomic DNA fragment, if present in the genome of the organism from which the DNA sample is obtained are located at multiple sites in the genome.

In certain embodiments, the array further comprises a second compartment or a second set of compartments, wherein a second primer pair specific to a second genomic DNA fragment in the test genomic DNA is contained in the second compartment or each of the second set of compartments, and wherein (a) the second genomic DNA fragment and (b) one or more fragments nearly identical to the second genomic DNA fragment, if present in the genome of the organism from which the DNA sample is obtained are located at multiple sites in the genome.

In certain embodiments, the array further comprises a third compartment or a third set of compartments, wherein a third primer pair specific to a third genomic DNA fragment in the test genomic DNA is contained in the third compartment or each of the third set of compartments, and wherein (a) the third genomic DNA fragment and (b) one or more fragments nearly identical to the third genomic DNA fragment, if present in the genome of the organism from which the DNA sample is obtained are located at multiple sites in the genome.

In certain embodiments, the array further comprises a fourth compartment or a fourth set of compartments, wherein a fourth primer pair specific to a fourth genomic DNA fragment in the test genomic DNA is present in the fourth compartment or each of the fourth set of compartments, and wherein (a) the fourth genomic DNA fragment and (b) one or more fragments nearly identical to the fourth genomic DNA fragment, if present in the genome of the organism from which the DNA sample is obtained are located at multiple sites in the genome.

In certain embodiments, the first, second, third, and fourth primer pairs if present in the array are selected from the following primer pairs: (1) SEQ ID NOS:1 and 2, (2) SEQ ID NOS:3 and 4, (3) SEQ ID NOS:5 and 6, (4) SEQ ID NOS:7 and 8, (5) SEQ ID NOS:9 and 10, (6) SEQ ID NOS:11 and 12, (7) SEQ ID NOS:13 and 14, (8) SEQ ID NOS:15 and 16, (9) SEQ ID NOS:17 and 18, (10) SEQ ID NOS:19 and 20, and (11) SEQ ID NOS:21 and 22, (12) SEQ ID NOS:23 and 24.

In another aspect, the present disclosure provides a kit for assessing the quality of a test genomic DNA sample, comprising: one or more primer pairs specific to one or more genomic DNA fragments in a test genomic DNA sample, wherein for each of the one or more genomic DNA fragments, (a) the genomic DNA fragment itself and (b) one or more fragments nearly identical to the genomic DNA fragment, if present in the genome of the organism from which the test genomic DNA sample is obtained, are located at multiple sites in the genome.

In certain embodiments, the number of the primer pairs is 4 to 8.

In a related aspect, the present disclosure provides a kit for assessing the quality of a test genomic DNA sample, comprising the array provided herein.

In certain embodiments, the kit further comprises a control genomic DNA sample.

In certain embodiments, the kit further comprises one or more reagents for performing real-time PCR.

BRIEF DESCRIPTION OF THE DRAWINGS

FIG. 1 shows a DNA quality control PCR array plate layout.

DETAILED DESCRIPTION

Figure 2:
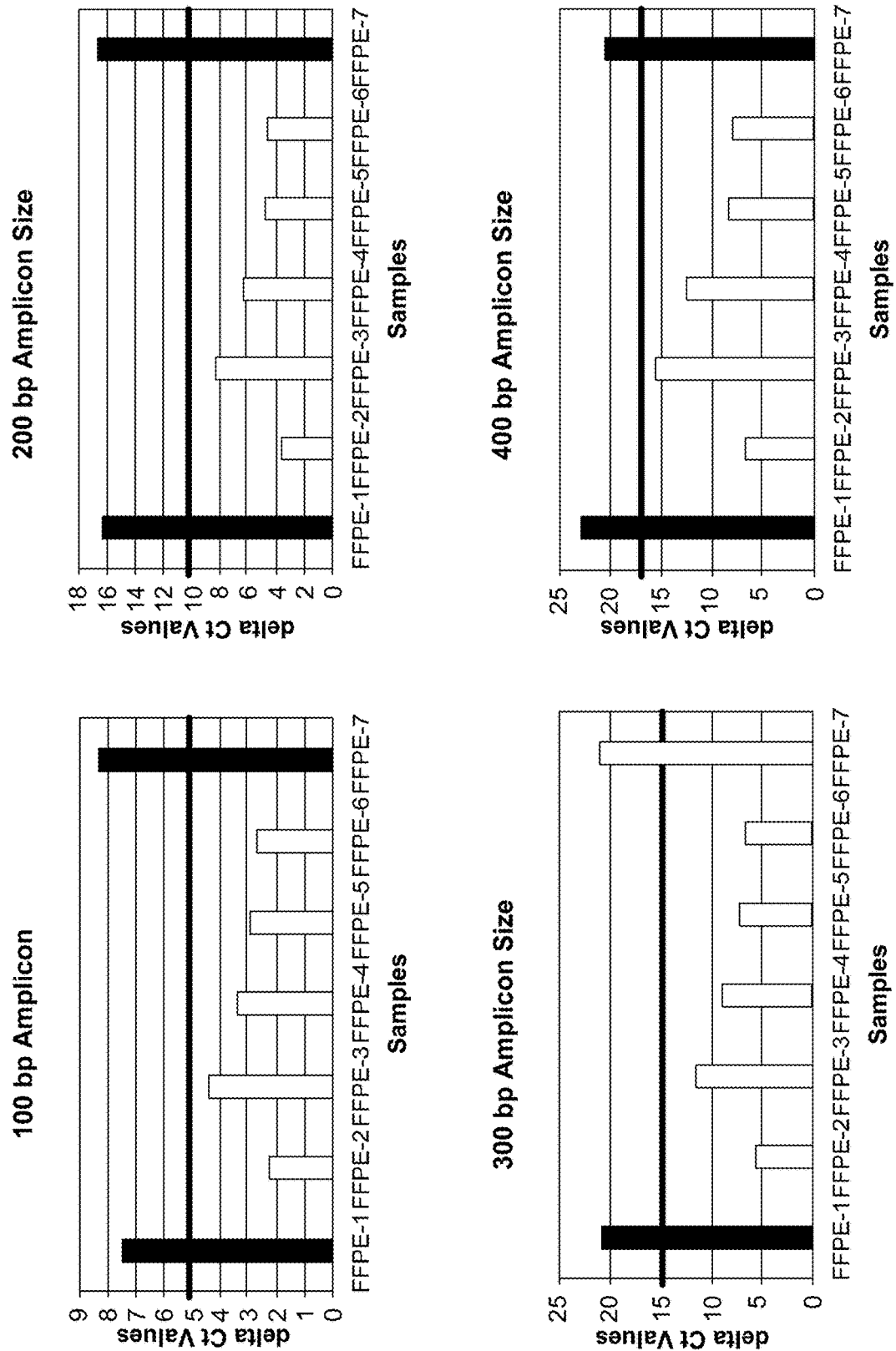
FIG. 2 shows correlation between results from DNA Quality Control (QC) Panel analysis and NGS sequencing results. FFPE samples that generated successful sequencing data are indicated by empty bars and those that did not are shown by solid bars.

The present disclosure provides methods, arrays and kits for assessing the quality of genomic DNA samples for downstream DNA analyses. The methods provided herein analyze regions in the genome from which a genomic DNA sample is obtained that have identical or nearly identical copies randomly distributed across multiple or all autosomes. By designing PCR assays for such regions, these methods assess sample DNA quality at many different chromosomal locations, and the performance of such PCR assays is thus less affected by genomic heterogeneity in the genomic DNA population in the sample. In addition, the PCR assays may optionally be designed to generate amplicons of different sizes. By comparing the performance of such PCR assays, the distribution of amplifiable fragment in the genomic DNA sample may be evaluated. This information can help design the optimal molecular assay for a sample with suboptimal quality.

In the following description, any ranges provided herein include all the values in the ranges unless otherwise indicated.

It should also be noted that the term "or" is generally employed in its sense including "and/or" (i.e., to mean either one, both, or any combination thereof of the alternatives) unless the content clearly dictates otherwise.

Also, as used in this specification and the appended claims, the singular forms "a," "an," and "the" include plural referents unless the content clearly dictates otherwise.

As used herein, "about" means±15% of the indicated range or value unless otherwise indicated.

Genomic DNA Samples

The term "DNA" refers to a polymer comprising deoxyribonucleosides that are covalently bonded, typically by phosphodiester linkages between subunits. This term includes but is not limited to genomic DNA (DNA in the genome of an organism), cDNA (DNA reversely transcribed from mRNA), and plasmid DNA.

A "genomic DNA sample" is a sample that comprises genomic DNA isolated from a source of interest.

Genomic DNA samples whose quality may be assessed by the methods provided herein include genomic DNA samples prepared from any samples that comprise genomic DNA. Exemplary samples from which genomic DNA samples may be prepared include, but are not limited to, blood, swabs, body fluid, tissues including but not limited to, liver, spleen, kidney, lung, intestine, brain, heart, muscle, pancreas, cell cultures, plant tissues or samples, as well as lysates, extracts, or materials and fractions obtained from the samples described above or any cells and microorganisms and viruses that may be present on or in a sample and the like.

Materials obtained from clinical or forensic settings that contain nucleic acids are also within the intended meaning of the term "sample" from which a genomic DNA sample may be prepared. Preferably, the sample is a biological sample derived from a human, animal, plant, bacteria or fungi. The term "sample" also includes processed samples including preserved, fixed and/or stabilized samples, such as formalin fixed and paraffin-embedded (FFPE samples) and other samples that were treated with cross-linking fixatives such as glutaraldehyde.

Genomic DNA samples whose quality may be assessed by the methods provided herein may be prepared from nucleic acid-containing samples by any methods known in the art. Exemplary methods include lysis of nucleic acid-containing samples followed by isolating genomic DNA using, for example, organic solvent such as phenol or nucleic acid binding columns. Genomic DNA samples may also be treated with RNase to reduce or eliminate RNA contamination.

Downstream Analyses

The methods for assessing the quality of genomic DNA samples provided herein are useful in determining whether a particular genomic DNA sample is suitable for downstream molecular analyses, including NGS and real-time PCR assays. Thus, various methods for assessing the quality of genomic DNA samples provided herein may further comprise performing one or more additional analyses of the genomic DNA samples whose quality has been assessed as suitable for such analysis. As described in detail below, assessing the quality of a genomic DNA sample includes determining amplification efficiency and size distribution of amplifiable fragments of the sample.

Methods for Assessing Genomic DNA Quality

The present disclosure provides a method for assessing the quality of a test genomic DNA sample, comprising: (a) performing one or more real-time PCR reactions that use genomic DNA in a test genomic DNA sample as templates in the presence of one or more primer pairs, wherein each of the one or more primer pairs is specific for amplifying identical or nearly identical genomic DNA fragments that are present at multiple locations in the genome of the organism from which the DNA sample is obtained, (b) performing one or more real-time PCR reactions that use genomic DNA in a control genomic DNA sample as templates in the presence of the one or more primer pairs used in step (a), (c) determining the Ct values for the one or more real-time PCR reactions in step (a), and (d) determining the Ct values for the one or more real-time PCR reactions in step (b), wherein the difference between the Ct values determined in step (c) and the corresponding Ct values determined in step (d) for the one or more real-time PCR reactions are indicative of the quality of the test genomic DNA sample.

The quality of a test genomic DNA sample refers to characteristics of the test genomic DNA sample related to downstream analyses of the sample, such as genomic DNA concentration, presence of contaminants, genomic DNA sizes, degree of degradation, presence of base damages, cross-linkage, or modifications, amplification efficiency, size distribution of amplifiable fragments, and the like.

A method for assessing the quality of a test genomic DNA sample provided herein may assess one or more characteristics of the test genomic DNA sample. For example, the method may be able to characterize the amplification efficiency of a test genomic DNA sample, and thus suggest appropriate amounts of the samples to be used in downstream analyses. The method may also be able to characterize the size distribution of amplifiable fragments, which may guide the design of downstream analyses to achieve optimal use of the sample.

The method provided herein uses one or more primer pairs each of which is specific for amplifying identical or nearly identical genomic DNA fragments that are present at multiple locations in the genome of the organism from which the genomic DNA sample is obtained. The presence of the identical or nearly identical genomic DNA fragments at multiple locations in the genome provides a broader representation of the genomic DNA population in the genomic DNA sample than a genomic DNA fragment present only at one location in the genome. Thus, the overall amplification performance using such primer pair(s) is less affected by genomic heterogeneity in the genomic DNA population of the sample.

For example, in the Example described below, the primer pair for Primer Assay No. 1 (SEQ ID NOS:1 and 2) is able to amplify a 111 bp genomic DNA fragment that is present in 20 locations in the human genome and another 110 bp nearly identical sequence at another location in the human genome. Thus, using this primer pair, genomic DNA amplification at 21 different locations in the human genome may be analyzed.

A genomic DNA fragment is nearly identical to another DNA if (a) the size difference between the two genomic DNA fragments is at most 5% (e.g., at most 4%, 3%, 2% or 1%) of the full length of the longer fragment, and (b) the sequence identity between the two fragments is at least 95% (e.g., at least 96%, 97%, 98%, or 99%).

Preferably, genomic DNA fragments amplified in the presence of a primer pair only have at most 4% differences in size and in sequence between each other. More preferably, genomic DNA fragments amplified in the presence of a primer pair only have at most 2% differences in size and in sequence between each other.

While any method known in the art for making such determinations may be used, for the purpose of the present invention, the BLAST algorithm described in Altschul et al., J. Mol. Biol. 215:403-410 (1990) and Karlin et al., PNAS USA 90:5873-5787 (1993) is used for determining sequence identity according to the methods of the invention. A particularly useful BLAST program is the WU-BLAST-2 program (Altschul et al., Methods in Enzymology 266:460-480 (1996)). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A percent nucleic acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

An "oligonucleotide" refers to a short polymer composed of deoxyribonucleotides, ribonucleotides or combinations thereof. Oligonucleotides are generally between about 10 to 100 nucleotides, preferably about 15 to 30 nucleotides, in length.

A "primer" for amplification is an oligonucleotide that is complementary to a target nucleotide sequence and leads to addition of nucleotides to the 3' end of the primer in the presence of a DNA or RNA polymerase.

A primer pair "specific for amplifying" a target sequence or a primer pair "specific to" a target sequence refers to a primer pair capable of specifically amplifying the target sequence.

"Specifically amplifying" a target sequence means amplifying the target sequence or a sequence that is nearly identical to the target sequence without amplifying other sequences in a reaction mixture.

A sequence that is "nearly identical" to a target sequence if the size difference between these two sequences are at most 5% of the longer fragment and the sequence identity between these two sequences is at least 95%.

The genomic DNA fragments amplified in the presence of a particular primer pair may be present at 5, 6, 7, 8, 9, 10, 11, 12, 13, 14, 15, 16, 17, 18, 19, 20, 21, 22, 23, 24, 25, 30, or more different locations in a genome of interest. They may be present at 2, 3, 4, 5, 6, 7, 8, 9, 10 or more different autosomes. Preferably, no more than 50%, 40%, 30% or 20% of the genomic DNA fragment amplified by the particular primer pair are located on a single chromosome.

The genomic DNA fragments amplified by multiple primer pairs may be present in more than 50%, 60%, 70%, 80%, 85%, 90%, or 95% of all autosomes of the organism from which a genomic DNA sample is obtained. Preferably, the genomic DNA fragments amplified are not present on sex chromosomes. Also preferably, no more than 50%, 40%, 30% or 20% of the genomic DNA fragment amplified by the multiple primer pairs are located on a single chromosome.

Primer pairs used in the method provided herein may be designed by identifying regions in a genome of interest regions that have identical or highly nearly identical copies distributed on different chromosomes using bioinformatic approach. Preferably, such regions do not contain known single nucleotide polymorphisms (SNPs), insertions or deletions (INDELs), repetitive sequences, or other variations.

The method provided herein may use 1, 2, 3, 4, 5, 6, 7, 8, 9, 10, 11, 12, or more primer pairs.

In one embodiment, two primer pairs may share a primer so that the shorter amplicons produced by one primer pair are completely within the longer amplicons produced by the other primer pair. This configuration allows evaluation of the frequency of random DNA damages occurred in the sample.

The genomic DNA fragments amplified by real-time PCR may be from about 60 to 600 bp, such as about 80, 100, 120, 140, 160, 180, 200, 220, 240, 260, 280, 300, 320, 340, 360, 380, 400, 450, 500, or 550 bp.

The sizes of the genomic DNA fragments amplified by different primer pairs may be the same or different. For example, a method provided herein may use primer pairs that generate amplicons that are about 100, 200, 300 and 400 bp. It is also contemplated that multiple primer pairs are used to produce amplicons of the same or a similar size. For example, the method in the Example used 12 primer pairs: a first set of 3 primer pairs amplified genomic DNA fragments of about 100 bp, a second set of 3 primer pairs amplified genomic DNA fragments of about 200 bp, a third set of 3 primer pairs amplified genomic DNA fragments of about 300 bp, and a fourth set of 3 primer pairs amplified genomic DNA fragments of about 400 bp. The use of primer pairs that amplify genomic DNA fragments of different sizes allows the evaluation of the distribution of amplifiable fragments in a genomic DNA sample, which in turn guides the best use of samples of inferior quality.

To ensure broad applicability of the method provided herein, the primer pairs may be tested to assess population variability. For example, if the method is for assessing the quality of human genomic DNA samples, candidate primer pairs may be used to analyze genomic DNA samples from different human populations to evaluate their consistency. If the method is for assessing the quality of mouse genomic DNA samples, candidate primer pairs may be used to analyze genomic DNA samples from different mouse strains.

In one embodiment, the method provided herein is to assess the quality of genomic DNA samples prepared from samples that contain human cells or tissues. The method may use one or more (e.g., 1, 2, 3, 4, 5, 6, 7, 8, 9, 10, 11, and 12) of the following primer pairs: (1) SEQ ID NOS:1 and 2, (2) SEQ ID NOS:3 and 4, (3) SEQ ID NOS:5 and 6, (4) SEQ ID NOS:7 and 8, (5) SEQ ID NOS:9 and 10, (6) SEQ ID NOS:11 and 12, (7) SEQ ID NOS:13 and 14, (8) SEQ ID NOS:15 and 16, (9) SEQ ID NOS:17 and 18, (10) SEQ ID NOS:19 and 20, (11) SEQ ID NOS:21 and 22, and (12) SEQ ID NOS:23 and 24). The sequences of such primer pairs are provided in the Example below.

When multiple primer pairs are used, each primer pair may be included in an individual real-time PCR reaction. Alternatively, multiple primer pairs may be included in a single real-time PCR reaction. For example, some primer pairs may be included in a single PCR reaction, and the other primer pairs may be included in one or more other PCR reactions. In one embodiment, two or more PCR primers that amplify genomic DNA fragments of the same or a similar size are included in a single PCR reaction. A genomic DNA fragment is of a similar size as another genomic DNA fragment if the difference between the two fragments is less than 5% (e.g., less than 4%, 3%, 2% or 1%) of the longer fragment.

Preferably, the test genomic DNA sample is from a sample that comprises human cells or tissue, such as a clinical sample. Exemplary preferred primer pairs for assessing the quality of human genomic DNA samples are provided in the Example.

A control genomic DNA sample is a genomic DNA sample isolated from a sample that contains cells or tissue from the same species as the sample from which a test genomic DNA sample is isolated. In addition, the control genomic DNA sample has been shown to be of high quality by, for example, real-time PCR, NGS or other analyses.

For example, if a method is to assess the quality of certain genomic DNA samples prepared from human FFPF tissues, a control genomic DNA sample may be a human genomic DNA sample prepared from human blood and has been shown to be of good quality (e.g., with high amplification efficiency and producing high quality NGS data).

"Real-time polymerase chain reaction (PCR)" (also referred to as "qPCR") refers to a type of PCR that amplifies and simultaneously quantify a target DNA molecule. Its key feature is that the amplified DNA is detected as the reaction progresses in real time.

Similar to traditional PCR reactions, real-time PCR reaction mixtures contain DNA polymerase, such as Taq DNA polymerase (e.g., hot-start Taq DNA polymerase), buffer, magnesium, dNTPs, and optionally other agents (e.g., stabilizing agents such as gelatin and bovine serum albumin). In addition, real-time PCR reaction mixtures also contain reagents for real time detection and quantification of amplification products.

For real-time detection and quantification, probes specific to amplification products may be detectably labeled with a fluorophore. Alternatively, the amplification reaction may be performed in the presence of an intercalating dye. Changes in fluorescence during the amplification reaction are monitored and are used in measuring the amount of amplification products.

Exemplary fluorophore-labeled probes include TAQ-MAN® probes. Such a probe is typically labeled with a reporter molecule such as a fluorescent dye at its 5' end and a quencher molecule at its 3' end. The close proximity of the reporter molecule to the quencher molecule prevents detection of its fluorescence. Breakdown of the probe by the 5' to 3' exonuclease activity of a DNA polymerase (e.g., Taq polymerase) breaks the reporter-quencher proximity and thus allows unquenched emission of fluorescence, which can be detected. An increase in the product targeted by the reporter probe at each PCR cycle therefore causes a proportional increase in fluorescence due to the breakdown of the probe and release of the reporter. Additional exemplary fluorophore-labeled probes similar to TAQMAN® probes include Molecular Beacon probes and Scorpion probes.

Exemplary intercalating dyes include SYBR® Green. Such a dye binds to all double-stranded DNA in PCR, causing fluorescence of the dye. An increase in DNA product during PCR thus leads to an increase in fluorescence intensity and is measured at each cycle, thus allowing DNA concentration to be quantified.

DNA quantification by real-time PCR may rely on plotting fluorescence against the number of cycles on a logarithmic scale. A threshold for detecting DNA-based fluorescence is set slightly above background. The number of cycles at which the fluorescence exceeds the threshold is called "the threshold cycle (Ct)."

Preferably, one or more real-time PCR reactions that use genomic DNA in a test genomic DNA sample as templates performed in step (a) of the method provided herein are performed under the same or similar conditions as the real-time PCR reactions that use genomic DNA in a control genomic DNA sample as templates are performed in step (b). For example, the real-time PCR reactions of steps (a) and (b) may be performed in reaction mixtures containing the same DNA polymerase in the same amount, the same PCR buffer, the same magnesium concentration, the same intercalating dye in the same amount if the intercalating dye is used for detection and quantification of amplification products, and the same dNTPs concentration and under the same thermocycling scheme.

Also preferably, the Ct values for the one or more real-time PCR reactions in step (a) determined in step (c) of the method provided herein are determined under the same or similar conditions as the Ct values for the one or more real-time PCR reactions in step (b) are determined in step (d). For example, the Ct determination in steps (c) and (d) may be performed using the same apparatus.

A Ct value determined in step (d) "corresponds to" a Ct value determined in step (c) if the Ct value determined in step (d) is obtained from a reaction mixture that contains the same primer pair or the same set of primer pairs as the reaction mixture from which the Ct value determined in step (c) is obtained. In other words, the Ct value determined in step (c) and the "corresponding" Ct value determined in step (d) are to quantify genomic DNA fragments amplified in the presence of the same primer pair or the same set of primer pairs.

The difference between a Ct value determined in step (c) and the corresponding Ct value determined in step (d) may be used to characterize or indicate the quality of the test genomic DNA sample. For example, the difference equal to or less than a predetermined value may indicate that the test genomic DNA sample is of high quality that is suitable for downstream analysis (e.g., qPCR and NGS), whereas the difference more than a predetermined value may indicate that the test genomic DNA sample is of low quality. The predetermined value for a given primer pair may be obtained using control samples and other samples for which downstream analyses have been performed.

If a method for assessing the quality of a test genomic DNA sample comprises amplifying genomic DNA fragments using multiple primer pairs, the Ct difference between real-time PCR reactions using genomic DNA in a test genomic DNA sample as templates and those using genomic DNA in a control genomic DNA sample as templates for each primer pair may be determined and used to characterize or indicate the quality of the test genomic DNA sample. In addition, the average of the Ct differences for the multiple primer pairs may be used to characterize or indicate the overall quality of the test genomic DNA sample.

The method for assessing the quality of a test genomic DNA sample may comprise amplifying genomic DNA fragments using multiple primer pairs that produce amplicons of the same or a substantially similar size but with substantially different sequences. Amplicons are similar in size if the size differences among these amplicons are less than about 25% of the longest amplicon. Amplicons are substantially different in sequences if sequence identities among these amplicons are less than about 50%. In such a case, the Ct difference between real-time PCR reactions using genomic DNA in a test genomic DNA sample as templates and those using genomic DNA in a control genomic DNA sample as templates for each primer pair may be determined and used to characterize or indicate the quality of the test genomic DNA sample. In addition, the average of the Ct differences for the multiple primer pairs may be used to characterize or indicate the quality of the test genomic DNA sample with respect to amplifying genomic DNA fragments that are similar in size as those amplified using the primer pairs. If the method also uses other primer pairs that amplify genomic DNA fragments that are substantially different in size from those described above, the average of the Ct differences for all the primer pairs used may be determined and used to characterize or indicate the overall quality of the test genomic DNA sample.

The method for assessing the quality of a genomic DNA sample may use multiple primer pairs that amplify genomic DNA fragments having at least 2, 3, 4, or 5 substantially different sizes. Two genomic DNA fragments are substantially different in size if their size difference is more than 50 bp, such as more than 75 bp, 100 bp, 125 bp, or 150 bp. For example, in the method described below in the Example, 12 primer pairs were used to produce genomic DNA fragments having 4 substantially different sizes: about 100 bp, about 200 bp, about 300 bp and about 400 bp.

Arrays for Assessing Genomic DNA Quality

The present disclosure also provides an array for assessing the quality of a DNA sample.

Figure 1:
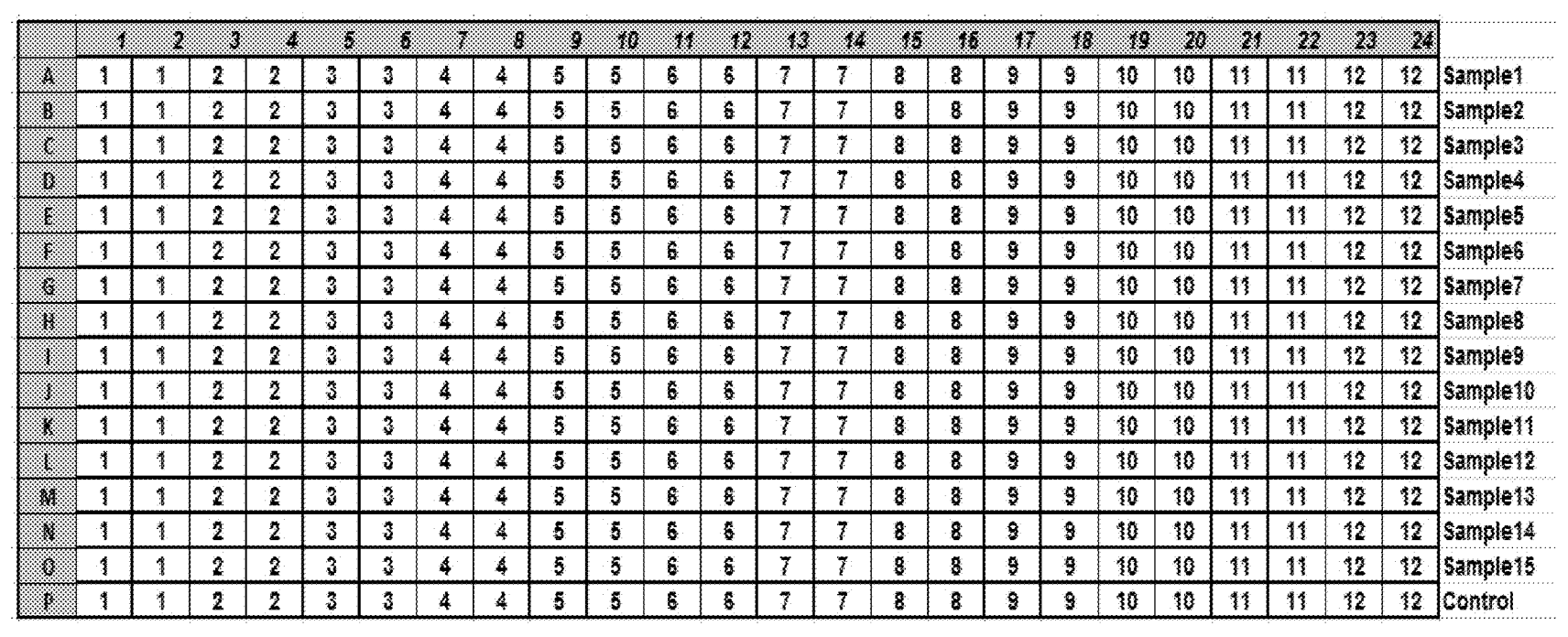

The array comprises a solid support and multiple compartments in the solid support. Exemplary arrays include multi-well plates, such as 96-well, 100-well, 384-well plates, and the like. The layout of an exemplary array is shown in FIG. 1.

The array provided herein may comprise a first primer pair specific to a first genomic DNA fragment in a test genomic DNA sample in a first compartment or each of a first set of compartments, and wherein (a) the first genomic DNA fragment and (b) one or more fragments nearly identical to the first genomic DNA fragment, if present in the genome of the organism from which the DNA sample is obtained are located at multiple sites in the genome.

The array may further comprise a second compartment or a second set of compartments, wherein a second primer pair specific to a second genomic DNA fragment in the test genomic DNA is contained in the second compartment or each of the second set of compartments, and wherein (a) the second genomic DNA fragment and (b) one or more fragments nearly identical to the second genomic DNA fragment, if present in the genome of the organism from which the DNA sample is obtained are located at multiple sites in the genome.

The array may further comprise a third compartment or a third set of compartments, wherein a third primer pair specific to a third genomic DNA fragment in the test genomic DNA is contained in the third compartment or each of the third set of compartments, and wherein (a) the third genomic DNA fragment and (b) one or more fragments nearly identical to the third genomic DNA fragment, if present in the genome of the organism from which the DNA sample is obtained are located at multiple sites in the genome.

The array may further comprise a fourth compartment or a fourth set of compartments, wherein a fourth primer pair specific to a fourth genomic DNA fragment in the test genomic DNA is present in the fourth compartment or each of the fourth set of compartments, and wherein (a) the fourth genomic DNA fragment and (b) one or more fragments nearly identical to the fourth genomic DNA fragment, if present in the genome of the organism from which the DNA sample is obtained are located at multiple sites in the genome.

The array may further comprise one or more (e.g., 2, 3, 4, 5, 6, 7, 8, 9, 10, 11, 12, 15, 18, 20, and 24) additional compartments or one or more (e.g., 2, 3, 4, 5, 6, 7, 8, 9, 10, 11, 12, 15, 18, 20, and 24) additional set of compartments that contain one or more (e.g., 2, 3, 4, 5, 6, 7, 8, 9, 10, 11, 12, 15, 18, 20, and 24) primer pairs. Each of the additional primer pairs is able to amplify identical or nearly identical genomic DNA fragments that are present at multiple sites in the genome of the organism from which the test genomic DNA sample is obtained.

If a set of compartments are present in an array that each contain the same primer pair, one of the compartments may contain, in addition to the primer pair, a portion of a control genomic DNA sample.

The primer pairs that may be included in the array provided herein and control genomic DNA samples are described above with respect to methods for assessing the quality of a test genomic DNA sample.

In a related aspect, the present disclosure also provides use of the array provided herein in assessing the quality of a genomic DNA sample, including determining suitability of using the genomic DNA sample in downstream analysis such as NGS and additional real-time PCR analysis and determining the size distribution of amplifiable fragments in the genomic DNA sample.

Kits for Assessing Genomic DNA Quality

The present disclosure also provides kits for assessing the quality of a genomic DNA sample.

The kit provided herein comprises one or more primer pairs specific to one or more genomic DNA fragments in a test genomic DNA sample, wherein for each of the one or more genomic DNA fragments, (a) the genomic DNA fragment itself and (b) one or more fragments nearly identical to the genomic DNA fragment, if present in the genome of the organism from which the test genomic DNA sample is obtained, are located at multiple sites in the genome. The number of the primer pairs in a kit may be 1, 2, 3, 4, 5, 6, 7, 8, 9, 10, 11, 12, 13, 14, 15, 16, 17, 18, 19, 20, 21, 22, 23, 24, or more.

The one or more primer pairs may be in an array format. Thus, the kit provided herein may comprise an array for assessing genomic DNA quality as described above.

The kit may further comprise a control genomic DNA sample.

The kit may further comprise one or more reagents for performing real-time PCR.

The reagents include buffer, magnesium, dNTPs, DNA polymerase (e.g., hot start polymerase), and other agents (e.g., stabilizing agents such as gelatin and bovine serum albumin). Some of the reagents (e.g., dNTPs, magnesium, and buffer) may be pre-mixed to form a PCR reaction mix that is included in the kit.

The primer pairs that may be included in the kit provided herein and control genomic DNA samples are described above with respect to methods for assessing the quality of a test genomic DNA sample.

In a related aspect, the present disclosure also provides use of the kit provided herein in assessing the quality of a genomic DNA sample, including determining suitability of using the genomic DNA sample in downstream analysis such as NGS and additional real-time PCR analysis and determining the size distribution of amplifiable fragments in the genomic DNA sample.

The following example is for illustration and is not limiting.

EXAMPLE

Using bioinformatic approach, more than a few hundred regions in the human genome that have identical or highly similar copies randomly distributed on different chromosomes were identified. Real-time PCR amplicons of approximately 100, 200, 300 and 400 bp were designed for most of them. Some shorter PCR amplicons were completely within other longer PCR amplicons, and two of the pairs share one common primer site. This configuration made it feasible to evaluate the frequency of random DNA damages occurred in the sample.

The performance of those PCR assays was verified in over a hundred normal human DNA samples representing different ethnic origins. 48 assays were selected based on the assay sensitivity and robustness in the tested population. Based on qPCR assay performance, 12 assays were selected for further evaluation.

For each of the 12 assays, the primer pair sequences, the number of sequences that the primer pair is able to amplify (referred to as "number of hits") in the human genome, hg19 (GRCh37 Genome Reference Consortium Human Reference 37 (GCA_000001405.1)), the size of the first hit, and the location of first hit are provided in Table 1 below:

TABLE 1

| Assay No. | Primer Sequence (5'→3') | SEQ ID NO: | No. of Hits | First Hit Size | First Hit Location |
|---|---|---|---|---|---|
| 1 | TGGTAGCTTGAGTCACTGTG GGATTTGGGCATAGGTTTG | 1 2 | 21 | 111 bp | chr11:135345 + 135455 |

TABLE 1-continued

| Assay No. | Primer Sequence (5'→3') | SEQ ID NO: | No. of Hits | First Hit Size | First Hit Location |
|---|---|---|---|---|---|
| 2 | ATGATGGATCTTTCCCAAC<br>TGACAAGTAAAGCTGGAATAATC | 3<br>4 | 24 | 103 bp | chr15:20140335 + 20140437 |
| 3 | TAAATCATCCACATACTGAAGGAC<br>ATAGCCCTCATCTGTTTGGTC | 5<br>6 | 25 | 92 bp | chr10:66540447 + 66540538 |
| 4 | TTCCCACACCAGTCTTCAC<br>GGATTTGGGCATAGGTTTG | 7<br>8 | 22 | 205 bp | chr11:135251 + 135455 |
| 5 | CCTCCCAAGTGTTCTGCTC<br>TGACAAGTAAAGCTGGAATAATC | 9<br>10 | 27 | 212 bp | chr15:20140226 + 20140437 |
| 6 | CCTTATTATCACCCTGCTCTC<br>CCTGTGGGTATTTCTAGTCG | 11<br>12 | 31* | 219 bp | chr10:99460360 + 99460578 |
| 7 | CCTCACTCCCTCACTCGAC<br>GGATTTGGGCATAGGTTTG | 13<br>14 | 27 | 309 bp | chr11:135147 + 135455 |
| 8 | TCACTCCCTCACTCGACAC<br>GGATTTGGGCATAGGTTTG | 15<br>16 | 27 | 307 bp | chr11:135149 + 135455 |
| 9 | TATAAAGGCACTAATCCCATTC<br>TTACATAGGACAGATGCAAATAGAC | 17<br>18 | 22 | 295 bp | chr15:20140175 + 20140469 |
| 10 | TCATCTGAGAAGGTGGAGC<br>GGATTTGGGCATAGGTTTG | 19<br>20 | 20 | 380 bp | chr11:135076 + 135455 |
| 11 | CAAATTCAGTGTTGATGAGAGC<br>TTACATAGGACAGATGCAAATAGAC | 21<br>22 | 26 | 399 bp | chr15:20140071 + 20140469 |
| 12 | GCCTCGTGGGATGAGAAAG<br>GCAGGGTGATAATAAGGAGAAG | 23<br>24 | 57* | 401 bp | chr10:99459976 + 99460376 |

*The numbers of hits for Assay Nos. 6 and 12 do not include 2 hits in unplaced contigs for Assay No. 6 or 3 hits in unplaced contigs for Assay No. 12.

For each assay, the oligonucleotide in the top row in the above table is the forward 5'-primer, whereas the oligonucleotide in the bottom row is the reverse 3'-primer.

The locations and sizes of the hits (that have perfect matches with 19 nucleotides at the 3' end of primers) for each of the twelve primer pairs are provided in Tables 2-13 below.

TABLE 2

Targets for Primer Assay No. 1

| Hit No. | Hit Location (hg19) | Hit Size (bp) |
|---|---|---|
| 1 | chr11: 135345+135455 | 111 |
| 2 | chr11: 131922+132032 | 111 |
| 3 | chr19: 205625+205735 | 111 |
| 4 | chr19: 202211+202321 | 111 |
| 5 | chr1: 243221121+243221231 | 111 |
| 6 | chr1: 675964+676074 | 111 |
| 7 | chr1: 672548+672658 | 111 |
| 8 | chr1: 669142+669251 | 110 |
| 9 | chr1: 665733+665843 | 111 |
| 10 | chr1: 140245+140355 | 111 |
| 11 | chr7: 56901226+56901336 | 111 |
| 12 | chr10: 38736084–38736194 | 111 |
| 13 | chr16: 90231916–90232026 | 111 |
| 14 | chr16: 90228497–90228607 | 111 |
| 15 | chr1: 323780–323890 | 111 |
| 16 | chr1: 320373–320483 | 111 |
| 17 | chr3: 197944687–197944797 | 111 |
| 18 | chr3: 197941273–197941383 | 111 |
| 19 | chr5: 180750395–180750505 | 111 |
| 20 | chr5: 180746988–180747098 | 111 |
| 21 | chr7: 128290584–128290694 | 111 |

TABLE 3

Targets for Primer Assay No. 2

| Hit No. | Hit Location (hg19) | Hit Size (bp) |
|---|---|---|
| 1 | chr15: 20140335+20140437 | 103 |
| 2 | chr16: 34178086+34178188 | 103 |
| 3 | chr16: 33844143+33844245 | 103 |
| 4 | chr16: 33061841+33061943 | 103 |
| 5 | chr16: 32118544+32118646 | 103 |
| 6 | chr2: 92265099+92265201 | 103 |
| 7 | chr2: 91988683+91988785 | 103 |
| 8 | chr2: 91661079+91661180 | 102 |
| 9 | chr2: 90439250+90439351 | 102 |
| 10 | chr7: 64575049+64575151 | 103 |
| 11 | chr7: 61675244+61675346 | 103 |
| 12 | chr9: 42734973+42735075 | 103 |
| 13 | chr10: 42604408–42604510 | 103 |
| 14 | chr16: 32831850–32831952 | 103 |
| 15 | chr21: 10893340–10893442 | 103 |
| 16 | chr2: 132804665–132804767 | 103 |
| 17 | chr2: 132765379–132765481 | 103 |
| 18 | chr2: 92240041–92240143 | 103 |
| 19 | chr7: 65046135–65046237 | 103 |
| 20 | chr7: 64983245–64983347 | 103 |
| 21 | chr7: 57937370–57937472 | 103 |
| 22 | chr9: 70411890–70411992 | 103 |
| 23 | chr9: 70160962–70161064 | 103 |
| 24 | chr9: 69795962–69796064 | 103 |

TABLE 4

Targets for Primer Assay No. 3

| Hit No. | Hit Location (hg19) | Hit Size (bp) |
|---|---|---|
| 1 | chr10: 66540447+66540538 | 92 |
| 2 | chr11: 101107279+101107370 | 92 |
| 3 | chr12: 95847668+95847759 | 92 |
| 4 | chr1: 94840246+94840337 | 92 |
| 5 | chr2: 218982552+218982643 | 92 |
| 6 | chr3: 44588305+44588396 | 92 |
| 7 | chr4: 35862674+35862765 | 92 |
| 8 | chr6: 87386987+87387078 | 92 |
| 9 | chr7: 151729234+151729325 | 92 |
| 10 | chr7: 23897603+23897694 | 92 |
| 11 | chr8: 87942626+87942717 | 92 |
| 12 | chr8: 54052020+54052111 | 92 |
| 13 | chr8: 42419179+42419270 | 92 |
| 14 | chr10: 121647046−121647137 | 92 |
| 15 | chr12: 131823434−131823525 | 92 |
| 16 | chr19: 8448392−8448483 | 92 |
| 17 | chr1: 161224222−161224313 | 92 |
| 18 | chr1: 105655701−105655792 | 92 |
| 19 | chr2: 98441604−98441695 | 92 |
| 20 | chr3: 190907594−190907685 | 92 |
| 21 | chr3: 164533317−164533408 | 92 |
| 22 | chr4: 45537496−45537587 | 92 |
| 23 | chr5: 114330130−114330221 | 92 |
| 24 | chr6: 38588227−38588318 | 92 |
| 25 | chr6: 16459961−16460052 | 92 |

TABLE 5

Targets for Primer Assay No. 4

| Hit No. | Hit Location (hg19) | Hit Size (bp) |
|---|---|---|
| 1 | chr11: 135251+135455 | 205 |
| 2 | chr11: 131828+132032 | 205 |
| 3 | chr19: 205531+205735 | 205 |
| 4 | chr19: 202117+202321 | 205 |
| 5 | chr1: 243221027+243221231 | 205 |
| 6 | chr1: 675870+676074 | 205 |
| 7 | chr1: 672454+672658 | 205 |
| 8 | chr1: 669048+669251 | 204 |
| 9 | chr1: 665639+665843 | 205 |
| 10 | chr1: 140151+140355 | 205 |
| 11 | chr7: 56446682+56446886 | 205 |
| 12 | chr7: 55816209+55816413 | 205 |
| 13 | chr16: 90231916−90232120 | 205 |
| 14 | chr16: 90228497−90228701 | 205 |
| 15 | chr1: 323780−323984 | 205 |
| 16 | chr1: 320373−320577 | 205 |
| 17 | chr3: 197944687−197944891 | 205 |
| 18 | chr3: 197941273−197941477 | 205 |
| 19 | chr5: 180750395−180750599 | 205 |
| 20 | chr5: 180746988−180747192 | 205 |
| 21 | chr7: 128290584−128290788 | 205 |
| 22 | chr7: 45846431−45846635 | 205 |

TABLE 6

Targets for Primer Assay No. 5

| Hit No. | Hit Location (hg19) | Hit Size (bp) |
|---|---|---|
| 1 | chr15: 20140226+20140437 | 212 |
| 2 | chr16: 34177977+34178188 | 212 |
| 3 | chr16: 33844034+33844245 | 212 |
| 4 | chr16: 33061732+33061943 | 212 |
| 5 | chr16: 32118435+32118646 | 212 |
| 6 | chr2: 92264990+92265201 | 212 |
| 7 | chr2: 91988574+91988785 | 212 |
| 8 | chr2: 91660970+91661180 | 211 |
| 9 | chr2: 90439141+90439351 | 211 |
| 10 | chr7: 64574941+64575151 | 211 |

TABLE 6-continued

Targets for Primer Assay No. 5

| Hit No. | Hit Location (hg19) | Hit Size (bp) |
|---|---|---|
| 11 | chr9: 42734864+42735075 | 212 |
| 12 | chr10: 42615575+42615786 | 212 |
| 13 | chr10: 42604408−42604618 | 211 |
| 14 | chr16: 46469617−46469827 | 211 |
| 15 | chr16: 46458916−46459127 | 212 |
| 16 | chr16: 32831850−32832061 | 212 |
| 17 | chr21: 10893340−10893551 | 212 |
| 18 | chr2: 132804665−132804876 | 212 |
| 19 | chr2: 132765379−132765590 | 212 |
| 20 | chr2: 92240041−92240252 | 212 |
| 21 | chr7: 65046135−65046345 | 211 |
| 22 | chr7: 64983245−64983455 | 211 |
| 23 | chr7: 61761699−61761910 | 212 |
| 24 | chr7: 57937370−57937581 | 212 |
| 25 | chr9: 70411890−70412101 | 212 |
| 26 | chr9: 70160962−70161173 | 212 |
| 27 | chr9: 69795962−69796173 | 212 |

TABLE 7

Targets for Primer Assay No. 6

| Hit No. | Hit Location (hg19) | Hit Size (bp) |
|---|---|---|
| 1 | chr10: 99460360+99460578 | 219 |
| 2 | chr10: 29716426+29716644 | 219 |
| 3 | chr12: 49510213+49510431 | 219 |
| 4 | chr13: 99417362+99417580 | 219 |
| 5 | chrUn_gl000223: 15304+15518 | 215 |
| 6 | chrUn_gl000223: 10365+10582 | 218 |
| 7 | chr1: 47599632+47599850 | 219 |
| 8 | chr2: 95857874+95858092 | 219 |
| 9 | chr4: 9668931+9669149 | 219 |
| 10 | chr4: 9132851+9133068 | 218 |
| 11 | chr4: 9124292+9124510 | 219 |
| 12 | chr5: 56843254+56843466 | 213 |
| 13 | chr6: 52748818+52749037 | 220 |
| 14 | chr8: 8063979+8064196 | 218 |
| 15 | chr9: 28880975+28881187 | 213 |
| 16 | chrX: 153750154+153750366 | 213 |
| 17 | chrX: 126488690+126488902 | 213 |
| 18 | chr11: 67597481−67597698 | 218 |
| 19 | chr11: 3468681−3468898 | 218 |
| 20 | chr12: 133672083−133672296 | 214 |
| 21 | chr12: 133667147−133667361 | 215 |
| 22 | chr13: 114947411−114947629 | 219 |
| 23 | chr15: 90889818−90890036 | 219 |
| 24 | chr2: 169418786−169418998 | 213 |
| 25 | chr3: 195454995−195455213 | 219 |
| 26 | chr4: 157307531−157307749 | 219 |
| 27 | chr4: 3987662−3987874 | 213 |
| 28 | chr4: 3979076−3979294 | 219 |
| 29 | chr5: 39828181−39828395 | 215 |
| 30 | chr7: 67568765−67568983 | 219 |
| 31 | chr7: 38270470−38270688 | 219 |
| 32 | chr8: 12316517−12316734 | 218 |
| 33 | chr8: 12073995−12074212 | 218 |

TABLE 8

Targets for Primer Assay No. 7

| Hit No. | Hit Location (hg19) | Hit Size (bp) |
|---|---|---|
| 1 | chr11: 135147+135455 | 309 |
| 2 | chr11: 131724+132032 | 309 |
| 3 | chr19: 205427+205735 | 309 |
| 4 | chr19: 202013+202321 | 309 |
| 5 | chr1: 243220923+243221231 | 309 |
| 6 | chr1: 222650846+222651154 | 309 |
| 7 | chr1: 675766+676074 | 309 |

TABLE 8-continued

Targets for Primer Assay No. 7

| Hit No. | Hit Location (hg19) | Hit Size (bp) |
|---|---|---|
| 8 | chr1: 672350+672658 | 309 |
| 9 | chr1: 668944+669251 | 308 |
| 10 | chr1: 665535+665843 | 309 |
| 11 | chr1: 140047+140355 | 309 |
| 12 | chr4: 120331644+120331952 | 309 |
| 13 | chr7: 56446578+56446886 | 309 |
| 14 | chr7: 55816105+55816413 | 309 |
| 15 | chr10: 38736084−38736392 | 309 |
| 16 | chr16: 90231916−90232224 | 309 |
| 17 | chr16: 90228497−90228805 | 309 |
| 18 | chr1: 323780−324088 | 309 |
| 19 | chr1: 320373−320681 | 309 |
| 20 | chr3: 197944687−197944995 | 309 |
| 21 | chr3: 197941273−197941581 | 309 |
| 22 | chr4: 119550936−119551244 | 309 |
| 23 | chr5: 180750395−180750703 | 309 |
| 24 | chr5: 180746988−180747296 | 309 |
| 25 | chr7: 128290584−128290892 | 309 |
| 26 | chr7: 45846431−45846739 | 309 |
| 27 | chr7: 39830686−39830993 | 308 |

TABLE 9

Targets for Primer Assay No. 8

| Hit No. | Hit Location (hg19) | Hit Size (bp) |
|---|---|---|
| 1 | chr11: 135149+135455 | 307 |
| 2 | chr11: 131726+132032 | 307 |
| 3 | chr19: 205429+205735 | 307 |
| 4 | chr19: 202015+202321 | 307 |
| 5 | chr1: 243220925+243221231 | 307 |
| 6 | chr1: 222650848+222651154 | 307 |
| 7 | chr1: 675768+676074 | 307 |
| 8 | chr1: 672352+672658 | 307 |
| 9 | chr1: 668946+669251 | 306 |
| 10 | chr1: 665537+665843 | 307 |
| 11 | chr1: 140049+140355 | 307 |
| 12 | chr4: 120331646+120331952 | 307 |
| 13 | chr7: 56446580+56446886 | 307 |
| 14 | chr7: 55816107+55816413 | 307 |
| 15 | chr10: 38736084−38736390 | 307 |
| 16 | chr16: 90231916−90232222 | 307 |
| 17 | chr16: 90228497−90228803 | 307 |
| 18 | chr1: 323780−324086 | 307 |
| 19 | chr1: 320373−320679 | 307 |
| 20 | chr3: 197944687−197944993 | 307 |
| 21 | chr3: 197941273−197941579 | 307 |
| 22 | chr4: 119550936−119551242 | 307 |
| 23 | chr5: 180750395−180750701 | 307 |
| 24 | chr5: 180746988−180747294 | 307 |
| 25 | chr7: 128290584−128290890 | 307 |
| 26 | chr7: 45846431−45846737 | 307 |
| 27 | chr7: 39830686−39830991 | 306 |

TABLE 10

Targets for Primer Assay No. 9

| Hit No. | Hit Location (hg19) | Hit Size (bp) |
|---|---|---|
| 1 | chr15: 20140175+20140469 | 295 |
| 2 | chr16: 33061681+33061975 | 295 |
| 3 | chr16: 32118384+32118678 | 295 |
| 4 | chr2: 91660919+91661212 | 294 |
| 5 | chr2: 90439090+90439383 | 294 |
| 6 | chr7: 64574890+64575183 | 294 |
| 7 | chr7: 61675084+61675378 | 295 |
| 8 | chr9: 42734813+42735107 | 295 |
| 9 | chr16: 46469585−46469878 | 294 |
| 10 | chr18: 15206512−15206806 | 295 |

TABLE 10-continued

Targets for Primer Assay No. 9

| Hit No. | Hit Location (hg19) | Hit Size (bp) |
|---|---|---|
| 11 | chr18: 15162997−15163291 | 295 |
| 12 | chr21: 10893308−10893602 | 295 |
| 13 | chr2: 132804633−132804927 | 295 |
| 14 | chr2: 132765347−132765641 | 295 |
| 15 | chr7: 65046103−65046396 | 294 |
| 16 | chr7: 64983213−64983506 | 294 |
| 17 | chr7: 61761667−61761961 | 295 |
| 18 | chr7: 61058228−61058522 | 295 |
| 19 | chr7: 57937338−57937632 | 295 |
| 20 | chr9: 70411858−70412152 | 295 |
| 21 | chr9: 70160930−70161224 | 295 |
| 22 | chr9: 69795930−69796224 | 295 |

TABLE 11

Targets for Primer Assay No. 10

| Hit No. | Hit Location (hg19) | Hit Size (bp) |
|---|---|---|
| 1 | chr11: 135076+135455 | 380 |
| 2 | chr11: 131653+132032 | 380 |
| 3 | chr19: 205356+205735 | 380 |
| 4 | chr19: 201942+202321 | 380 |
| 5 | chr1: 675695+676074 | 380 |
| 6 | chr1: 672279+672658 | 380 |
| 7 | chr1: 668873+669251 | 379 |
| 8 | chr1: 665464+665843 | 380 |
| 9 | chr1: 139976+140355 | 380 |
| 10 | chr7: 56446507+56446886 | 380 |
| 11 | chr7: 55816034+55816413 | 380 |
| 12 | chr16: 90231916−90232295 | 380 |
| 13 | chr16: 90228497−90228876 | 380 |
| 14 | chr1: 323780−324159 | 380 |
| 15 | chr1: 320373−320752 | 380 |
| 16 | chr3: 197944687−197945066 | 380 |
| 17 | chr3: 197941273−197941652 | 380 |
| 18 | chr5: 180750395−180750774 | 380 |
| 19 | chr5: 180746988−180747367 | 380 |
| 20 | chr7: 45846431−45846810 | 380 |

TABLE 12

Targets for Primer Assay No. 11

| Hit No. | Hit Location (hg19) | Hit Size (bp) |
|---|---|---|
| 1 | chr15: 20140071+20140469 | 399 |
| 2 | chr16: 33061577+33061975 | 399 |
| 3 | chr16: 32118280+32118678 | 399 |
| 4 | chr2: 92264835+92265233 | 399 |
| 5 | chr2: 91988419+91988817 | 399 |
| 6 | chr2: 91660815+91661212 | 398 |
| 7 | chr2: 90438986+90439383 | 398 |
| 8 | chr7: 64574786+64575183 | 398 |
| 9 | chr7: 61674980+61675378 | 399 |
| 10 | chr9: 42734709+42735107 | 399 |
| 11 | chr10: 42604376−42604773 | 398 |
| 12 | chr16: 46469585−46469982 | 398 |
| 13 | chr18: 15206512−15206910 | 399 |
| 14 | chr18: 15162997−15163395 | 399 |
| 15 | chr21: 10893308−10893706 | 399 |
| 16 | chr2: 132804633−132805031 | 399 |
| 17 | chr2: 132765347−132765745 | 399 |
| 18 | chr2: 92240009−92240407 | 399 |
| 19 | chr7: 65046103−65046500 | 398 |
| 20 | chr7: 64983213−64983610 | 398 |
| 21 | chr7: 61761667−61762065 | 399 |
| 22 | chr7: 61058228−61058626 | 399 |
| 23 | chr7: 57937338−57937736 | 399 |
| 24 | chr9: 70411858−70412256 | 399 |

TABLE 12-continued

Targets for Primer Assay No. 11

| Hit No. | Hit Location (hg19) | Hit Size (bp) |
|---|---|---|
| 25 | chr9: 70160930−70161328 | 399 |
| 26 | chr9: 69795930−69796328 | 399 |

TABLE 13

Targets for Primer Assay No. 12

| Hit No. | Hit Location (hg19) | Hit Size (bp) |
|---|---|---|
| 1 | chr10: 99459976+99460376 | 401 |
| 2 | chr10: 98163398+98163798 | 401 |
| 3 | chr10: 33183786+33184184 | 399 |
| 4 | chr11: 123150791+123151191 | 401 |
| 5 | chr11: 67689132+67689532 | 401 |
| 6 | chr11: 37952518+37952918 | 401 |
| 7 | chr12: 49509829+49510229 | 401 |
| 8 | chr13: 43285312+43285712 | 401 |
| 9 | chr21: 39945179+39945579 | 401 |
| 10 | chr22: 17540425+17540825 | 401 |
| 11 | chrUn_gl000223: 14920+15320 | 401 |
| 12 | chrUn_gl000223: 9981+10381 | 401 |
| 13 | chrUn_gl000231: 22879+23279 | 401 |
| 14 | chr1: 236668200+236668600 | 401 |
| 15 | chr1: 47599249+47599648 | 400 |
| 16 | chr1: 40937804+40938204 | 401 |
| 17 | chr2: 95857490+95857890 | 401 |
| 18 | chr3: 75587273+75587673 | 401 |
| 19 | chr4: 122318082+122318482 | 401 |
| 20 | chr4: 9753064+9753464 | 401 |
| 21 | chr4: 4076419+4076819 | 401 |
| 22 | chr5: 161797510+161797907 | 398 |
| 23 | chr6: 52748434+52748834 | 401 |
| 24 | chr7: 104789485+104789885 | 401 |
| 25 | chr8: 12423891+12424287 | 397 |
| 26 | chr8: 8063597+8063995 | 399 |
| 27 | chr9: 131612897+131613292 | 396 |
| 28 | chr9: 129479179+129479579 | 401 |
| 29 | chr9: 28880591+28880991 | 401 |
| 30 | chrX: 153749772+153750170 | 399 |
| 31 | chrX: 90425667+90426067 | 401 |
| 32 | chr10: 96957178−96957577 | 400 |
| 33 | chr11: 118879040−118879439 | 400 |
| 34 | chr11: 71384933−71385333 | 401 |
| 35 | chr11: 67597682−67598080 | 399 |
| 36 | chr11: 23114276−23114676 | 401 |
| 37 | chr11: 3468882−3469280 | 399 |
| 38 | chr12: 133672280−133672680 | 401 |
| 39 | chr12: 133667345−133667745 | 401 |
| 40 | chr12: 8584230−8584630 | 401 |
| 41 | chr13: 114947613−114948011 | 399 |
| 42 | chr14: 106487687−106488087 | 401 |
| 43 | chr15: 98172559−98172959 | 401 |
| 44 | chr15: 90890020−90890420 | 401 |
| 45 | chr1: 113359623−113360023 | 401 |
| 46 | chr3: 142471114−142471514 | 401 |
| 47 | chr3: 98081627−98082027 | 401 |
| 48 | chr3: 15187255−15187655 | 401 |
| 49 | chr4: 157307733−157308132 | 400 |
| 50 | chr4: 43003876−43004276 | 401 |
| 51 | chr5: 154023434−154023835 | 402 |
| 52 | chr5: 152177074−152177473 | 400 |
| 53 | chr6: 52812723−52813123 | 401 |
| 54 | chr6: 43207456−43207860 | 405 |
| 55 | chr7: 67568967−67569365 | 399 |
| 56 | chr8: 12316718−12317116 | 399 |
| 57 | chr8: 12074196−12074594 | 399 |
| 58 | chr8: 7556947−7557347 | 401 |
| 59 | chr8: 7098403−7098803 | 401 |
| 60 | chr8: 6984728−6985128 | 401 |

The locations and sizes of additional hits with less stringent criteria (i.e., having perfect matches with 15 nucleotides at the 3' end of primers) for some of the twelve primer pairs are provided in Table 14 below.

TABLE 14

Additional Targets for Primer Assays

| Assay No. | Additional Hit No. | Hit Location (hg19) | Hit Size (bp) |
|---|---|---|---|
| 2 | 1 | chr1: 149030745+149030847 | 103 |
|   | 2 | chr7: 53197939−53198041 | 103 |
| 3 | 1 | chr16: 57432726+57432817 | 92 |
|   | 2 | chr8: 39738896+39738987 | 92 |
|   | 3 | chrX: 111355904+111355995 | 92 |
|   | 4 | chr17: 50654589−50654680 | 92 |
|   | 5 | chr17: 26042855−26042946 | 92 |
|   | 6 | chr2: 148072985−148073076 | 92 |
|   | 7 | chr4: 185659639−185659730 | 92 |
|   | 8 | chr5: 99320377−99320468 | 92 |
| 5 | 1 | chr21: 9475041+9475252 | 212 |
| 6 | 1 | chr10: 33184168+33184386 | 219 |
|   | 2 | chr11: 123151175+123151393 | 219 |
|   | 3 | chr12: 8417305−8417523 | 219 |
|   | 4 | chr15: 40936175−40936393 | 219 |
|   | 5 | chr1: 147181566−147181784 | 219 |
| 8 | 1 | chr7: 56901030+56901336 | 307 |
|   | 2 | chr7: 51460780+51461085 | 306 |
| 9 | 1 | chr7: 53197907−53198201 | 295 |
| 10 | 1 | chr1: 243220852+243221231 | 380 |
|   | 2 | chr1: 222650775+222651154 | 380 |
|   | 3 | chr4: 120331573+120331952 | 380 |
|   | 4 | chr7: 51460707+51461085 | 379 |
|   | 5 | chr10: 38736084−38736463 | 380 |
|   | 6 | chr4: 119550936−119551315 | 380 |
|   | 7 | chr7: 128290584−128290963 | 380 |
| 12 | 1 | chr2: 94434+94835 | 402 |
|   | 2 | chr5: 24466249+24466649 | 401 |
|   | 3 | chrY: 10013901+10014301 | 401 |
|   | 4 | chr10: 102793517−102793917 | 401 |
|   | 5 | chr11: 3416009−3416409 | 401 |
|   | 6 | chr14: 20709942−20710342 | 401 |
|   | 7 | chr16: 10923540−10923940 | 401 |
|   | 8 | chr2: 702776−703176 | 401 |
|   | 9 | chr3: 121330178−121330561 | 384 |
|   | 10 | chr4: 128360853−128361253 | 401 |
|   | 11 | chr4: 122367400−122367800 | 401 |
|   | 12 | chr4: 3907275−3907674 | 400 |

Methods for Performing PCR Assay

Genomic DNA was extracted from human FFPE samples (normal human genomic DNA from Promega (Cat. No. G304X, 90% of the DNA is longer than 50 kb in size as measured by pulsed-field gel electrophoresis) was used as control). 1-2 ng of genomic DNA was used in each PCR reaction. DNA Quality Control (QC) PCR Array and Qiagen RT² Real-Timer SYBR Green/ROX PCR Mix were used to perform PCR. The 12 primer pair assays of the DNA QC PCR Array were predispensed in 384-well PCR plate as layout in FIG. 1.

Methods for Performing Next Generation Sequencing

Briefly, a multiplexed PCR assay that targeted 400 amplicons was developed for target enrichment. Primers were designed to avoid known SNPs and repetitive sequences. 20 ng of normal human genomic DNA or genomic DNA isolated from FFPE samples were evaluated for multiplexed PCR based target enrichment. PCR enriched samples were subjected to NGS library construction with Ion Xpress Plus Fragment Library Kit. After quantification with GeneRead Library Quantification Array, template (library) dilution factor was determined for each sample. Appropriately diluted prepared NGS libraries were sequenced on Ion Torrent PGM sequencer according to Life Technologies' user guide.

In a preliminary study, DNA from seven FFPE samples of varying quality and control Universal DNA were analyzed in duplicate by real-time PCR using 12 selected qPCR primer assays. The average Ct values of all three sets of 100 bp, 200 bp, 300 bp and 400 bp amplicons were determined for each DNA sample. The average Ct value of specific amplicon size for the control DNA was subtracted from average Ct value of that amplicon size for FFPE DNA.

The resulting ΔCt values were plotted against the outcome of sequencing results (FIG. 2). Samples with ΔCt values lower than 5, 10, 15 and 17 with 100 bp, 200 bp, 300 bp and 400 bp amplicons, respectively, showed good sequencing results (FIG. 2). This suggests that selected 12 qPCR primer assays can be used to pre-qualify DNA samples for successful sequencing results.

Figure 3:
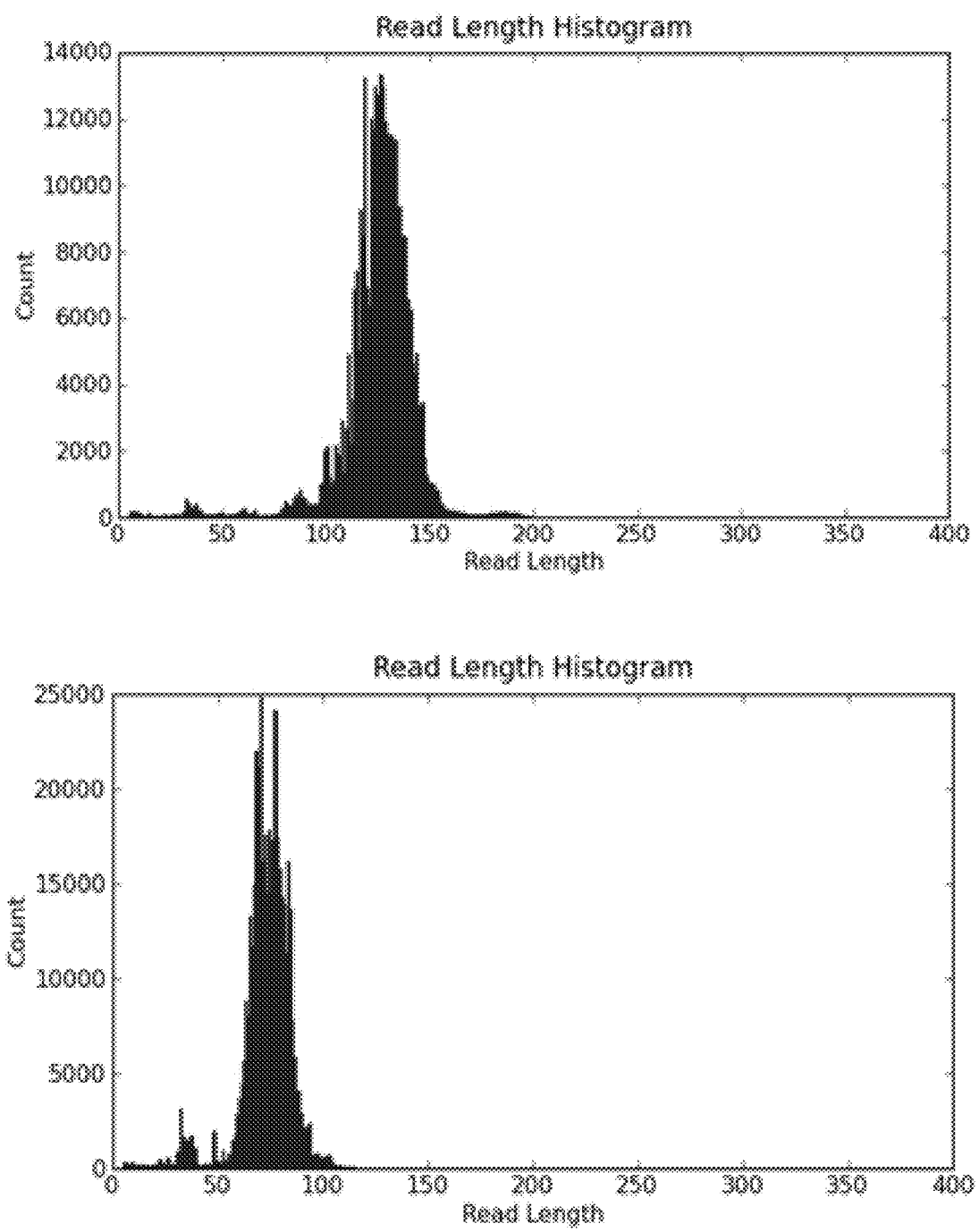
FIG. 3 shows the FFPE-1 sample's amplicon bias toward smaller read. The left graph is a read length histogram of control genomic DNA, and the right graph is a read length histogram of the FFPE-1 sample.

Five out of seven FFPE samples generated successful sequencing results. One sample (FFPE-1) generated smaller read length as compared to control universal DNA as well as other analyzed samples (FIG. 3), suggesting low quality of starting DNA with a potential risk of amplicon bias. The FFPE-7 sample showed insufficient amount of amplifiable library molecules upon qPCR based library quantification, after NGS library preparation, and did not process for sequencing.

Assuming that the higher the library dilution factor, the better the quality of DNA, samples with successful sequencing results were ranked for DNA quality as shown in Table 15 below. In addition, the average Ct value for the 12 assays of DNA QC Array was used to rank the DNA quality, assuming that the lower the averaged Ct value, the higher the quality rank. Interestingly, quality ranks based on the library dilution factors and based on the DNA QC Array analysis are the same. This suggests that the DNA QC Array analysis may be useful for recommending appropriate DNA input amount for NGS.

TABLE 15

| Samples | Library dilution factor | Quality rank based on dilution factor | Quality rank based on DNA QC Panel results |
|---|---|---|---|
| FFPE-2 | 16.0 | 1 | 1 |
| FFPE-3 | 4.3 | 5 | 5 |
| FFPE-4 | 10.5 | 4 | 4 |
| FFPE-5 | 12.3 | 3 | 3 |
| FFPE-6 | 14.8 | 2 | 2 |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for assessing the quality of a test genomic DNA sample for a downstream molecular DNA analysis, comprising:
   (a) performing one or more real-time PCR reactions that use genomic DNA in a test genomic DNA sample as templates in the presence of two or more primer pairs, wherein each of the two or more primer pairs is specific for amplifying identical or nearly identical genomic DNA fragments that are present at 10 or more different locations in the genome of the organism from which the test genomic DNA sample is obtained, wherein a genomic DNA fragment is nearly identical to another DNA if (i) the size difference between the two genomic DNA fragments is at most 5% of the full length of the longer fragment, and (ii) the sequence identity between the two fragments is at least 95%,
   (b) performing one or more real-time PCR reactions that use genomic DNA in a control genomic DNA sample as templates in the presence of the two or more primer pairs used in step (a),
   (c) determining the Ct values for the one or more real-time PCR reactions in step (a),
   (d) determining the Ct values for the one or more real-time PCR reactions in step (b),
   e) determining the difference (ΔCt) between the Ct values determined in step (c) and the corresponding Ct values determined in step (d) for the one or more real-time PCR reactions, wherein the difference is indicative of the quality of the test genomic DNA sample, and
   (f) performing one or more additional molecular analyses of the genomic DNA test sample whose quality has been assessed as suitable for such analysis.

2. The method of claim 1, wherein the method comprises: measuring PCR amplifiable molecules in the test genomic DNA sample using the difference in the Ct values (ΔCt) between the test genomic DNA sample determined in step (c) and the control genomic DNA sample determined in step (d); and/or determining the input amount of test genomic DNA for real-time PCR reactions based on the ΔCt.

3. The method of claim 1, having one or more of the following characteristics:
   i) the genomic DNA fragments amplified by multiple primer pairs are present in more than 50%, 60%, 70% or more than 80% of all autosomes of the organism from which the DNA sample is obtained;
   ii) the genomic DNA fragments amplified are not present on sex chromosomes;
   iii) no more than 50 percent, 40 percent, 30 percent or 20 percent of the genomic DNA fragment amplified by the multiple primer pairs are located on a single chromosome;
   iv) the genomic DNA fragments amplified in step (a) are between about 100 to 400 bp in length;
   v) the genomic DNA fragments amplified in the presence of a particular primer pair are present at 3 or more different autosomes; and/or
   vi) the number of the primer pairs is 2-12 or 4-8.

4. The method of claim 1, wherein
   i) the test genomic DNA sample is obtained from human cells or tissue,
   ii) the test genomic DNA sample is obtained from a clinical human cells or tissue sample, and/or
   iii) the test genomic DNA sample is obtained from a formalin fixed and paraffin-embedded (FFPE) sample.

5. The method of claim 1, wherein the genomic DNA fragments amplified in step (a) are of at least 2 substantially different sizes, wherein two genomic DNA fragments are substantially different in size if their size difference is more than 50 bp or more than 75 bp.

6. The method according to claim 5, wherein the method includes determining amplification efficiency and amount or size distribution of amplifiable fragments of the sample.

7. The method according to claim 5, wherein the method comprises comparing the performance of PCR assays generating amplicons of different sizes and evaluating the distribution of amplifiable fragments in the genomic DNA sample.

8. The method of claim 1, wherein multiple real-time PCR reactions are performed in each of steps (a) and (b), and the average difference between the Ct values determined in step (c) and the corresponding Ct values determined in step (d) for two or more of the multiple real-time PCR reactions is used to assess the quality of the test genomic DNA sample.

9. The method of claim 1, wherein the two or more primer pairs are selected from the primer pairs consisting of: (1) SEQ ID NOS:1 and 2, (2) SEQ ID NOS:3 and 4, (3) SEQ ID NOS:5 and 6, (4) SEQ ID NOS:7 and 8, (5) SEQ ID NOS:9 and 10, (6) SEQ ID NOS:11 and 12, (7) SEQ ID NOS:13 and 14, (8) SEQ ID NOS:15 and 16, (9) SEQ ID NOS:17 and 18, (10) SEQ ID NOS:19 and 20, (11) SEQ ID NOS:21 and 22, and (12) SEQ ID NOS:23 and 24.

10. The method of claim 1, wherein the organism for which the test genomic DNA sample is obtained is human, and wherein the identical or nearly identical genomic DNA fragments of step (a) are selected from the targets with chromosomal locations shown in Tables 2-14.

11. The method of claim 1, further comprising performing additional real-time PCR and/or NGS analysis of the test genomic DNA sample and wherein optionally, the input amount of the test genomic DNA sample in the additional real-time PCR is determined based on the difference between the Ct values determined in step (c) and the corresponding Ct values determined in step (d) for the one or more real-time PCR reactions.

12. The method according to claim 1, wherein each primer pair is included in an individual real-time PCR reaction or wherein multiple primer pairs are included in a single real-time PCR reaction.

13. The method according to claim 1, wherein assessing the quality of a genomic DNA sample includes determining amplification efficiency and amount or size distribution of amplifiable DNA fragments in the sample.

14. The method of claim 1, wherein an array is used in step (a) and/or step (b),
wherein the array comprises a solid support and multiple compartments in the solid support, wherein a first primer pair specific to a first genomic DNA fragment in the test genomic DNA sample is contained in a first compartment or each of a first set of compartments, and wherein (a) the first genomic DNA fragment and (b) one or more fragments nearly identical to the first genomic DNA fragment, if present in the genome of the organism from which the DNA sample is obtained, are located at 10 or more different locations in the genome of the organism from which the test genomic DNA sample is obtained,
the array optionally further comprising a second compartment or a second set of compartments, wherein a second primer pair specific to a second genomic DNA fragment in the test genomic DNA is contained in the second compartment or each of the second set of compartments, and wherein (a) the second genomic DNA fragment and (b) one or more fragments nearly identical to the second genomic DNA fragment, if present in the genome of the organism from which the DNA sample is obtained are located at 10 or more different locations in the genome of the organism from which the test genomic DNA sample is obtained, and wherein a genomic DNA fragment is nearly identical to another DNA if (i) the size difference between the two genomic DNA fragments is at most 5% of the full length of the longer fragment, and (ii) the sequence identity between the two fragments is at least 95%.

15. The method of claim 14, wherein the array further comprises a third compartment or a third set of compartments, wherein a third primer pair specific to a third genomic DNA fragment in the test genomic DNA is contained in the third compartment or each of the third set of compartments, and wherein (a) the third genomic DNA fragment and (b) one or more fragments nearly identical to the third genomic DNA fragment, if present in the genome of the organism from which the DNA sample is obtained are located at multiple sites in the genome, the array optionally further comprising also a fourth compartment or a fourth set of compartments, wherein a fourth primer pair specific to a fourth genomic DNA fragment in the test genomic DNA is present in the fourth compartment or each of the fourth set of compartments, and wherein (a) the fourth genomic DNA fragment and (b) one or more fragments nearly identical to the fourth genomic DNA fragment, if present in the genome of the organism from which the DNA sample is obtained, are located at multiple sites in the genome.

16. The method of claim 14, wherein the first primer pair and the second primer pair, if present, in the array are selected from the primer pairs consisting of: (1) SEQ ID NOS:1 and 2, (2) SEQ ID NOS:3 and 4, (3) SEQ ID NOS:5 and 6, (4) SEQ ID NOS:7 and 8, (5) SEQ ID NOS:9 and 10, (6) SEQ ID NOS:11 and 12, (7) SEQ ID NOS:13 and 14, (8) SEQ ID NOS:15 and 16, (9) SEQ ID NOS:17 and 18, (10) SEQ ID NOS:19 and 20, (11) SEQ ID NOS:21 and 22, and (12) SEQ ID NOS:23 and 24.

17. The method of claim 1, wherein the two or more primer pairs are comprised in a kit, and
wherein optionally:
(i) the number of the primer pairs is 2 to 12 or 4 to 8;
(ii) the kit comprises an array, wherein the array comprises a solid support and multiple compartments in the solid support, wherein a first primer pair specific to a first genomic DNA fragment in the test genomic DNA sample is contained in a first compartment or each of a first set of compartments, and wherein (a) the first genomic DNA fragment and (b) one or more fragments nearly identical to the first genomic DNA fragment, if present in the genome of the organism from which the DNA sample is obtained, are located at 10 or more different locations in the genome of the organism from which the test genomic DNA sample is obtained,
the array optionally further comprising a second compartment or a second set of compartments, wherein a second primer pair specific to a second genomic DNA fragment in the test genomic DNA is contained in the second compartment or each of the second set of compartments, and wherein (a) the second genomic DNA fragment and (b) one or more fragments nearly identical to the second genomic DNA fragment, if present in the genome of the organism from which the DNA sample is obtained are located at 10 or more different locations in the genome of the organism from which the test genomic DNA sample is obtained, and wherein a genomic DNA fragment is nearly identical to another DNA if (i) the size difference between the two genomic DNA fragments is at most 5% of the full length of the longer fragment, and (ii) the sequence identity between the two fragments is at least 95%;
(iii) the kit further comprises a control genomic DNA sample; and/or
(iv) the kit further comprises one or more reagents for performing real-time PCR.

18. The method of claim 3, having characteristic v), wherein no more than 50 percent, 40 percent, 30 percent or 20 percent of the genomic DNA fragment amplified by the particular primer pair are located on a single chromosome.

* * * * *

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Primer sequence

<400> SEQUENCE: 1
tggtagcttg agtcactgtg                                             20

<210> SEQ ID NO 2
<211> LENGTH: 19
<212> TYPE: DNA
<213> ORGANISM: Artificial Sequence
<220> FEATURE:
<223> OTHER INFORMATION: Primer sequence

<400> SEQUENCE: 2
ggatttgggc ataggtttg                                              19

<210> SEQ ID NO 3
<211> LENGTH: 19
<212> TYPE: DNA
<213> ORGANISM: Artificial Sequence
<220> FEATURE:
<223> OTHER INFORMATION: Primer sequence

<400> SEQUENCE: 3
atgatggatc tttcccaac                                              19
```

```
<210> SEQ ID NO 4
<211> LENGTH: 23
<212> TYPE: DNA
<213> ORGANISM: Artificial Sequence
<220> FEATURE:
<223> OTHER INFORMATION: Primer sequence

<400> SEQUENCE: 4
tgacaagtaa agctggaata atc                                              23

<210> SEQ ID NO 5
<211> LENGTH: 24
<212> TYPE: DNA
<213> ORGANISM: Artificial Sequence
<220> FEATURE:
<223> OTHER INFORMATION: Primer sequence

<400> SEQUENCE: 5
taaatcatcc acatactgaa ggac                                             24

<210> SEQ ID NO 6
<211> LENGTH: 21
<212> TYPE: DNA
<213> ORGANISM: Artificial Sequence
<220> FEATURE:
<223> OTHER INFORMATION: Primer sequence

<400> SEQUENCE: 6
atagccctca tctgtttggt c                                                21

<210> SEQ ID NO 7
<211> LENGTH: 19
<212> TYPE: DNA
<213> ORGANISM: Artificial Sequence
<220> FEATURE:
<223> OTHER INFORMATION: Primer sequence

<400> SEQUENCE: 7
ttcccacacc agtcttcac                                                   19

<210> SEQ ID NO 8
<211> LENGTH: 19
<212> TYPE: DNA
<213> ORGANISM: Artificial Sequence
<220> FEATURE:
<223> OTHER INFORMATION: Primer sequence

<400> SEQUENCE: 8
ggatttgggc ataggtttg                                                   19

<210> SEQ ID NO 9
<211> LENGTH: 19
<212> TYPE: DNA
<213> ORGANISM: Artificial Sequence
<220> FEATURE:
<223> OTHER INFORMATION: Primer sequence

<400> SEQUENCE: 9
cctcccaagt gttctgctc                                                   19

<210> SEQ ID NO 10
<211> LENGTH: 23
<212> TYPE: DNA
<213> ORGANISM: Artificial Sequence
<220> FEATURE:
<223> OTHER INFORMATION: Primer sequence
```

<400> SEQUENCE: 10
tgacaagtaa agctggaata atc                                    23

<210> SEQ ID NO 11
<211> LENGTH: 21
<212> TYPE: DNA
<213> ORGANISM: Artificial Sequence
<220> FEATURE:
<223> OTHER INFORMATION: Primer sequence

<400> SEQUENCE: 11
ccttattatc accctgctct c                                      21

<210> SEQ ID NO 12
<211> LENGTH: 20
<212> TYPE: DNA
<213> ORGANISM: Artificial Sequence
<220> FEATURE:
<223> OTHER INFORMATION: Primer sequence

<400> SEQUENCE: 12
cctgtgggta tttctagtcg                                        20

<210> SEQ ID NO 13
<211> LENGTH: 19
<212> TYPE: DNA
<213> ORGANISM: Artificial Sequence
<220> FEATURE:
<223> OTHER INFORMATION: Primer sequence

<400> SEQUENCE: 13
cctcactccc tcactcgac                                         19

<210> SEQ ID NO 14
<211> LENGTH: 19
<212> TYPE: DNA
<213> ORGANISM: Artificial Sequence
<220> FEATURE:
<223> OTHER INFORMATION: Primer sequence

<400> SEQUENCE: 14
ggatttgggc ataggtttg                                         19

<210> SEQ ID NO 15
<211> LENGTH: 19
<212> TYPE: DNA
<213> ORGANISM: Artificial Sequence
<220> FEATURE:
<223> OTHER INFORMATION: Primer sequence

<400> SEQUENCE: 15
tcactccctc actcgacac                                         19

<210> SEQ ID NO 16
<211> LENGTH: 19
<212> TYPE: DNA
<213> ORGANISM: Artificial Sequence
<220> FEATURE:
<223> OTHER INFORMATION: Primer sequence

<400> SEQUENCE: 16
ggatttgggc ataggtttg                                         19

<210> SEQ ID NO 17
<211> LENGTH: 22

<212> TYPE: DNA
<213> ORGANISM: Artificial Sequence
<220> FEATURE:
<223> OTHER INFORMATION: Primer sequence

<400> SEQUENCE: 17
tataaaggca ctaatcccat tc                                          22

<210> SEQ ID NO 18
<211> LENGTH: 25
<212> TYPE: DNA
<213> ORGANISM: Artificial Sequence
<220> FEATURE:
<223> OTHER INFORMATION: Primer sequence

<400> SEQUENCE: 18
ttacatagga cagatgcaaa tagac                                       25

<210> SEQ ID NO 19
<211> LENGTH: 19
<212> TYPE: DNA
<213> ORGANISM: Artificial Sequence
<220> FEATURE:
<223> OTHER INFORMATION: Primer sequence

<400> SEQUENCE: 19
tcatctgaga aggtggagc                                              19

<210> SEQ ID NO 20
<211> LENGTH: 19
<212> TYPE: DNA
<213> ORGANISM: Artificial Sequence
<220> FEATURE:
<223> OTHER INFORMATION: Primer sequence

<400> SEQUENCE: 20
ggatttgggc ataggtttg                                              19

<210> SEQ ID NO 21
<211> LENGTH: 22
<212> TYPE: DNA
<213> ORGANISM: Artificial Sequence
<220> FEATURE:
<223> OTHER INFORMATION: Primer sequence

<400> SEQUENCE: 21
caaattcagt gttgatgaga gc                                          22

<210> SEQ ID NO 22
<211> LENGTH: 25
<212> TYPE: DNA
<213> ORGANISM: Artificial Sequence
<220> FEATURE:
<223> OTHER INFORMATION: Primer sequence

<400> SEQUENCE: 22
ttacatagga cagatgcaaa tagac                                       25

<210> SEQ ID NO 23
<211> LENGTH: 19
<212> TYPE: DNA
<213> ORGANISM: Artificial Sequence
<220> FEATURE:
<223> OTHER INFORMATION: Primer sequence

<400> SEQUENCE: 23

```
gcctcgtggg atgagaaag                                                    19

<210> SEQ ID NO 24
<211> LENGTH: 22
<212> TYPE: DNA
<213> ORGANISM: Artificial Sequence
<220> FEATURE:
<223> OTHER INFORMATION: Primer sequence

<400> SEQUENCE: 24
gcagggtgat aataaggaga ag                                                22
```